(12) United States Patent
Grossman

(10) Patent No.: US 11,191,858 B2
(45) Date of Patent: Dec. 7, 2021

(54) SYSTEMS AND METHODS FOR TREATING ARTIFICIAL TURF

(71) Applicant: Allied Bioscience, Inc., Plano, TX (US)

(72) Inventor: Gavri Grossman, Plano, TX (US)

(73) Assignee: ALLIED BIOSCIENCE, INC., Plano, TX (US)

( * ) Notice: Subject to any disclaimer, the term of this patent is extended or adjusted under 35 U.S.C. 154(b) by 250 days.

(21) Appl. No.: 16/657,772

(22) Filed: Oct. 18, 2019

(65) Prior Publication Data
US 2020/0121816 A1 Apr. 23, 2020

Related U.S. Application Data

(60) Provisional application No. 62/747,734, filed on Oct. 19, 2018.

(51) Int. Cl.
*A61L 2/16* (2006.01)
*A01G 20/43* (2018.01)
*E01C 13/08* (2006.01)

(52) U.S. Cl.
CPC ............... *A61L 2/16* (2013.01); *A01G 20/43* (2018.02); *E01C 13/08* (2013.01)

(58) Field of Classification Search
CPC ....... A01G 20/30; A01G 20/43; A61L 2/0082; A61L 2/16; A61L 2/22; E01C 13/08
See application file for complete search history.

(56) References Cited

U.S. PATENT DOCUMENTS

| | | | |
|---|---|---|---|
| 8,307,487 B2 * | 11/2012 | Dairon ................... | A01G 20/43 15/21.1 |
| 10,889,946 B1 * | 1/2021 | Mast ....................... | E01C 23/06 |
| 2002/0134869 A1 * | 9/2002 | Pfisterer ................. | A01G 20/43 241/101.76 |
| 2011/0010879 A1 * | 1/2011 | Dairon ................... | A01G 20/43 15/105 |
| 2011/0079968 A1 * | 4/2011 | Murphy ................. | A01G 20/30 280/6.155 |
| 2013/0192633 A1 * | 8/2013 | Gil ......................... | A01G 20/43 134/6 |
| 2014/0130275 A1 * | 5/2014 | Peters .................... | A01G 20/43 15/88.4 |
| 2014/0265011 A1 * | 9/2014 | Mashburn ............... | C08J 11/06 264/176.1 |
| 2016/0271285 A1 * | 9/2016 | Weller .................... | A61L 2/10 |
| 2017/0258011 A1 * | 9/2017 | Owegeser ............... | B07B 1/30 |

(Continued)

FOREIGN PATENT DOCUMENTS

| | | | | | |
|---|---|---|---|---|---|
| EP | 2082918 A1 | * | 7/2009 | .......... | A01D 34/006 |
| EP | 2679723 A1 | * | 1/2014 | ............ | E01C 13/08 |
| EP | 3479667 A1 | * | 5/2019 | ............ | A01G 20/47 |

*Primary Examiner* — Marc Carlson
(74) *Attorney, Agent, or Firm* — Snell & Wilmer L.L.P.

(57) ABSTRACT

A method of reducing or preventing the transfer of pathogens between individuals interacting on artificial turf comprises treating the various components of the artificial turf with a residual antimicrobial coating composition. Treating the artificial turf comprises moving an artificial turf treatment apparatus over the turf in at least one pass, the apparatus being capable of liberating particles of infill material out from between the plastic blades of grass of the artificial turf and spraying the particles with the residual antimicrobial coating composition while the particles are in the air above the turf.

20 Claims, 1 Drawing Sheet

(56) References Cited

U.S. PATENT DOCUMENTS

| | | | |
|---|---|---|---|
| 2017/0260704 A1* | 9/2017 | De Geyter | A46B 13/001 |
| 2017/0347522 A1* | 12/2017 | Bissonnette | A01D 34/37 |
| 2018/0264511 A1* | 9/2018 | Wadkins | E01C 19/4866 |
| 2019/0166773 A1* | 6/2019 | Coleman | A01G 20/43 |

* cited by examiner

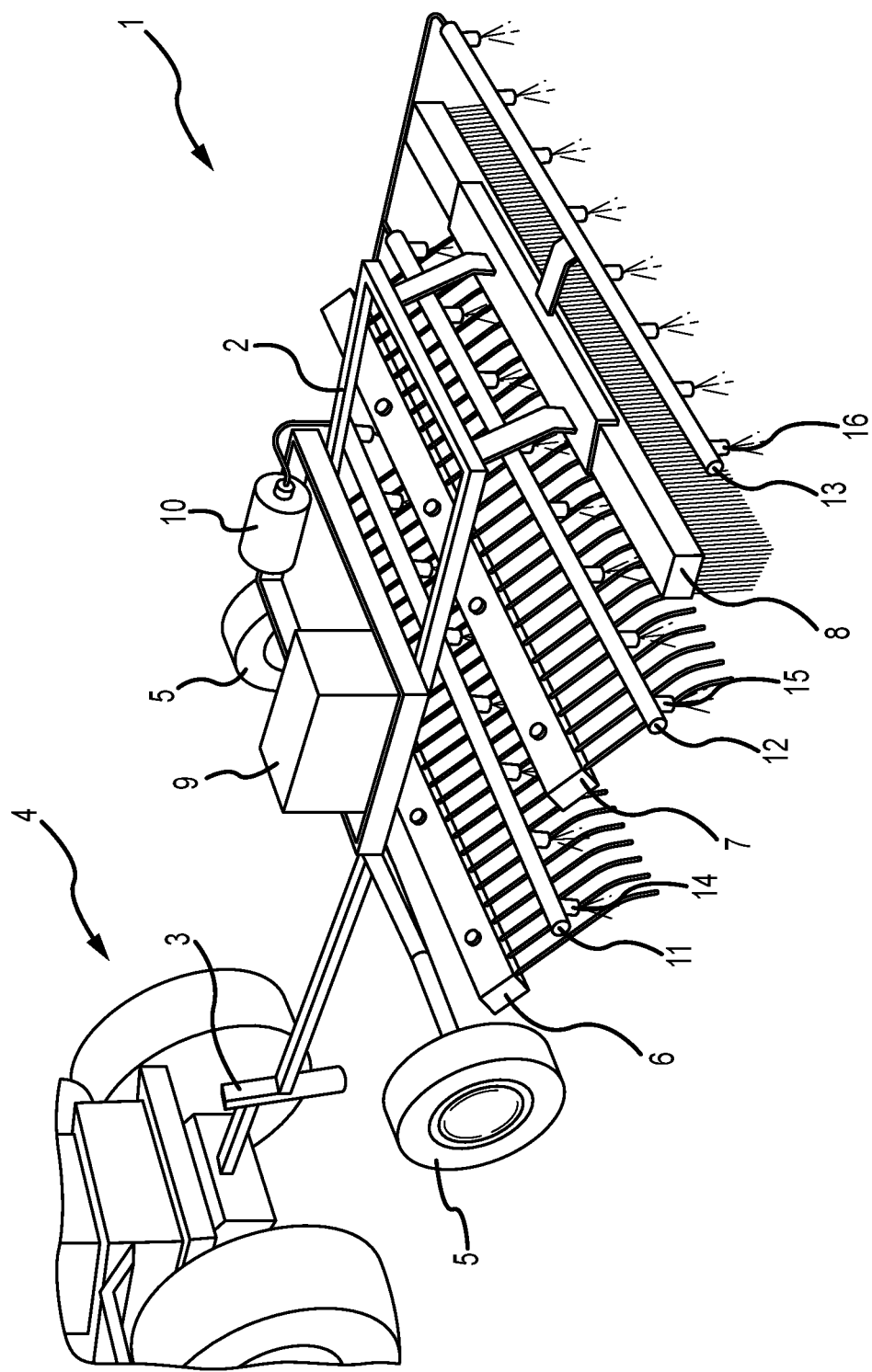

SYSTEMS AND METHODS FOR TREATING ARTIFICIAL TURF

CROSS-REFERENCE TO RELATED APPLICATIONS

This application claims priority to and the benefit of U.S. Provisional Patent Application Ser. No. 62/747,734 filed Oct. 19, 2018 and entitled "SYSTEMS AND METHODS FOR TREATING ARTIFICIAL TURF," the disclosure of which is incorporated herein by reference in its entirety.

FIELD

The present disclosure generally relates to controlling microorganisms on synthetic surfaces, and in particular to systems and methods for treating artificial turfs with cleaners, disinfectants, and residual antimicrobial agents to control the spread of pathogens.

BACKGROUND

In general, pathogens can be transferred from a contaminated surface to an individual, or between individuals through the intervention of a contaminated surface. In the simplest scenario, an infectious individual carrying a pathogen contaminates a surface with the pathogen and the second individual contacts the surface and acquires the infection. The surface aiding the pathogen transfer can be just about anything (e.g., a doorknob, a faucet handle, an elevator button, and so forth) recognized by most as being frequently handled. However, a surface also facilitating the transfer of pathogens between individuals can be a flooring-type surface (e.g., a yoga mat, an athletic pad, a carpet, a rug, tile or other hard surface, and most notably, artificial turf). Other surfaces in the spotlight include play balls that are found in bounce houses and fast-food restaurants for children to play in.

Artificial turf, due to its fibrous construction, synthetic components, deep voids, and possible infill materials, presents a uniquely challenging surface on which to control pathogen transfer. Artificial turf is now found in thousands of sporting event fields of all types and sizes, where it is used in place of real grass. Some institutions are newly built with artificial turf, while other existing facilities may have converted from real grass to an artificial turf.

A wide variety of pathogens (e.g., bacteria, viruses, and fungi) are potentially transferred between athletes during an athletic event played on artificial turf. For example, pathogens commonly transferred between athletes include various *Staphylococcus* species of bacteria, including methicillin-resistant *Staphylococcus aureus* (MRSA). Transfer of blood-borne pathogens is also of great concern in sporting events where players are frequently injured and bleeding, including such organisms as hepatitis B, hepatitis C, and human immunodeficiency virus (HIV). The complex structure and variety of generally hydrophobic synthetic materials of artificial turf help the survival of pathogens, such as for example, by shielding UV radiation and by resisting wetting and cleaning. Further, very large fields of artificial turf, such as found in a football stadium, are simply too large to clean and sanitize with detergent products, such as one might consider doing for a small piece of artificial turf in a residential backyard.

Given the unique construction of artificial turf, its widespread use in sporting facilities of all kinds, and its ability to participate in pathogen transfer between individuals interacting with the artificial turf, new systems and methods are needed to treat artificial turfs of all kinds, such as to prevent the transfer of pathogens between athletes on a playing field comprising artificial turf.

SUMMARY

In various embodiments, systems and methods for treating artificial turf are provided. In various embodiments, a method of treating artificial turf comprises applying various cleaners and disinfectants to the turf using a sprayer, such as an agricultural sprayer. In other embodiments, a system for treating artificial turf comprises an artificial turf treatment apparatus usable for treating artificial turf with an antimicrobial composition and optionally other materials, and a method of treating artificial turf to reduce or prevent pathogen transfer between individuals interacting on the artificial turf, such as players in a sporting event played on a field of the artificial turf.

In various embodiments, an artificial turf treatment apparatus is used for treating artificial turf with an antimicrobial composition, such as to provide a residual antimicrobial coating on various surfaces of the artificial turf construct. In various examples, an artificial turf treatment apparatus comprises an agitating module and a spraying module. In various embodiments, the artificial turf treatment apparatus further comprises a hitch module configured to hitch the apparatus behind a tractor or other machine in order to conveniently cover wide expanses of artificial turf. In general, the agitating module physically disturbs the artificial turf in a predetermined manner and the spraying module disposes an antimicrobial composition onto and into the artificial turf at particular times and in particular patterns of distribution.

In various embodiments, the agitating module of the artificial turf treatment apparatus comprises any combination of brooms, brushes, or rakes, or constituents thereof, such as bristles and/or tines. The spraying portion of the apparatus comprises an electrostatic sprayer. In various embodiments, the apparatus may further comprise a surface energy treatment module usable to treat the various synthetic components of artificial turf and change the surface energy and wettability of those components. In some examples, the surface treatment module is separate from the spraying module, and comprises an ozone generator, or where practical, corona discharge. In various examples, the spraying module of the apparatus is be used to treat the various surfaces of artificial turf with a surface modifying agent (e.g., ozone) distributed through the spraying module, possibly eliminating the need for a separate surface treatment spraying system. Surface modification may be conducted just prior to spraying the artificial turf with a residual antimicrobial coating composition via the spraying module.

In various embodiments, a method of reducing or preventing transfer of pathogens in a sporting event played on artificial turf comprises the steps of agitating the artificial turf and spraying an antimicrobial composition onto and into the artificial turf. In various embodiments, the two steps of agitating and spraying may be repeated any number of times. Further, the agitating and spraying steps may be conducted in either order, or simultaneously, and in any combination in the event agitating and spraying are conducted more than one time. In various embodiments, an artificial turf treatment apparatus comprising an agitating module and a spraying module is used to carry out a method of preventing transfer of pathogens in a sporting event played on a field of artificial turf by treating the artificial turf on which the sporting event is to be played with an antimicrobial composition.

In various embodiments, artificial turf comprises both a fibrous portion anchored into a base material and at least one infill material within the interstices between fibers. The infill material may comprise any combination of sand and/or synthetic particles, such as rubber particles. In these instances, a method of treating the artificial turf with an antimicrobial composition comprises agitating the artificial turf in such a way that at least a portion of at least one of the infill materials is liberated out from the interstices of the fibrous portion of the artificial turf so that the infill material can be coated with the antimicrobial composition. In various embodiments, an apparatus comprising an agitating portion and a spraying portion is moved over the artificial turf wherein the infill material is agitated into the air at least some distance off the top of the artificial grass blades where the infill material is impinged with a spray of antimicrobial composition from the sprayer portion of the apparatus.

In various embodiments, an artificial turf treatment apparatus comprises: an agitating module capable of liberating particulate infill material out from the artificial turf and a spraying module capable of applying a chemical composition to the artificial turf. In some instances, the apparatus further comprises an optional surface energy treatment module and a hitch. In certain examples, the surface energy treatment module comprises an ozone generator and optionally an oxygen source for the generator.

The agitating module may comprise at least one of a broom or a rake. In various examples, the agitating module comprises bristles, tines, or combinations thereof. In some instances, the agitating module comprises a tow-behind or push-in-front sweeper further comprising a rotating drum of bristles.

In various embodiments, the artificial turf particulate infill material is selected from the group consisting of silica sand, cryogenic rubber, crumb rubber, and combinations thereof.

In various embodiments, the spraying module comprises at least one tank capable of storing and dispensing the chemical composition, a fluidic pump, a spray nozzle, a chemical transfer tubing placing the tank and the fluidic pump in fluidic communication, and a chemical transfer tubing placing the fluidic pump and the spray nozzle in fluidic communication such that the chemical composition is dispensed from the tank and out the spray nozzle when the fluidic pump is operating.

In various embodiments, the spraying module comprises an electrostatic spray system.

In various embodiments, the chemical composition comprises any combination of cleaners, sanitizers and disinfectants, such as for example, soaps and detergents, and quaternary, oxygen, alcohol, chlorine or any other type of disinfectant. In other embodiments, the chemical composition comprises a residual sanitizing coating composition comprising an organosilane selected from the group consisting of 3-(trimethoxysilyl) propyl dimethyl octadecyl ammonium chloride, 3-(trihydroxysilyl) propyl dimethyl octadecyl ammonium chloride, 3-chloropropyltrimethoxysilane, 3-chloropropylsilanetriol, 3-aminopropyltriethoxysilane, 3-aminopropylsilanetriol, homopolymers thereof, and mixtures thereof.

In various embodiments, a method of applying cleaners and disinfectants to artificial turf comprises applying the desired composition or combination of compositions to the turf using an agricultural sprayer. In other embodiments, a method of applying a chemical composition to particles of infill material in artificial turf comprises liberating the particles out from the artificial turf and spraying the particles while the particles are temporarily suspended above the artificial turf. The step of liberating the particles of infill material further comprises the action of bristles or tines on the particles. In various embodiments, the chemical composition comprises a residual antimicrobial coating composition.

In various embodiments, the bristles are organized on a rotating drum of a sweeper. The action of the bristles or the tines on the particles of infill material may further comprise movement of the bristles or the tines through the artificial turf.

In various embodiments, the artificial turf may comprise synthetic plastic blades of grass bonded to a base material, and wherein the particles of infill material are disposed between the synthetic plastic blades of grass. Infill material may comprise any combination of silica sand, cryogenic rubber, and crumb rubber.

In various embodiments, a method of applying a chemical composition to particles of infill material may also comprise the step of surface energy treating a portion of a surface of at least one of the synthetic plastic blades of grass, the base material, or the particles of infill material prior to the step of spraying. In various aspects, artificial turf may be conditioned prior to treatment with a residual antimicrobial coating composition. The prior conditioning may comprise any combination of cleaning, sanitizing, disinfecting and surface energy treatment.

In various embodiments, a method of reducing or preventing the transfer of pathogens between individuals interacting on artificial turf comprises treating the artificial turf with a residual antimicrobial coating composition. In some instances, the pathogen may be any one or combination of hepatitis B virus, hepatitis C virus, human immunodeficiency virus (HIV), norovirus, poliovirus, rotavirus, influenza virus, adenovirus, *Staphylococcus aureus*, methicillin resistant *Staphylococcus aureus* (MRSA), vancomycin resistant *Enterococcus* (VRE), carbapenem resistant Enterobacteriacea (CRE), *Listeria* spp., *Klebsiella* spp., *Pseudomonas aeruginosa, Acinetobacter* ssp., *Bacillus* anthraces, *Salmonella* spp., *Campylobacter* spp., *Mycobacterium* spp., *Streptococcus* spp., *Clostridium difficile, Herpes gladiatorum, Herpes rugbiorum, Tinea pedis*, and *Tinea cruris*. The precise identity of the pathogen or pathogens destroyed or at least mitigated on artificial turf depends on the compositions applied and, in some instances, the presence of pre-cleaning of the turf and the order of application of the various materials to the turf.

In various embodiments, the artificial turf comprises synthetic plastic blades of grass bonded to a base material and particles of infill material disposed between the synthetic plastic blades of grass, wherein the infill material is selected from the group consisting of silica sand, cryogenic rubber, crumb rubber, and combinations thereof.

In various embodiments, the step of treating the artificial turf with a residual antimicrobial coating comprises moving an artificial turf treatment apparatus over the artificial turf at least one time, the artificial turf treatment apparatus comprising an agitating module capable of liberating the particles of infill material out from between the synthetic blades of grass, a spraying module capable of spraying at least one of the synthetic plastic blades of grass, the base material, or the particles of infill material with the residual antimicrobial coating composition, and optionally a surface energy treatment module capable of reducing the surface energy of at least a portion of a surface of at least one of the synthetic plastic blades of grass, the base material, or the particles of infill material.

In various embodiments, the artificial turf treatment apparatus is moved at least two passes over the artificial turf, wherein at least one pass over the artificial turf provides any combination of cleaning, sanitizing, disinfecting and surface energy treatment of at least one portion of at least one surface of one of the synthetic plastic blades of grass, the base material, or the particles of infill material, and wherein at least one pass over the artificial turf provides spraying of one of the synthetic plastic blades of grass, the base material, or the particles of infill material with the residual antimicrobial coating composition.

In various embodiments, the step of treating the artificial turf with a residual antimicrobial coating further comprises liberating the particles of infill material out from between the synthetic plastic blades of grass and the spraying of the particles of infill material with the residual antimicrobial coating composition while the particles of infill material are temporarily out from between the synthetic plastic blades of grass.

In various embodiments, the agitating module comprises bristles, tines, or combinations thereof.

In various embodiments, the spraying module comprises at least one tank capable of storing and dispensing the chemical composition, a fluidic pump, a spray nozzle, a chemical transfer tubing placing the tank and the fluidic pump in fluidic communication, and a chemical transfer tubing placing the fluidic pump and the spray nozzle in fluidic communication such that the chemical composition is dispensed from the tank and out the spray nozzle when the fluidic pump is operating.

In various embodiments, the surface energy treatment module comprises an ozone generator.

In various embodiments, treatment of artificial turf comprises applying any combination of cleaners, sanitizers, and disinfectants. Such products may comprise synthetic detergents, or hydrogen peroxide-based, alcohol-based or chlorine-based sanitizers and disinfectants. In certain aspects, treatment of artificial turf may include any number of rinsing procedures, such as after a treatment with a detergent.

In various embodiments, the residual antimicrobial coating composition comprises an organosilane and optionally an organic amine, the organosilane may be selected from the group consisting of 3-(trimethoxysilyl) propyl dimethyl octadecyl ammonium chloride, 3-(trihydroxysilyl) propyl dimethyl octadecyl ammonium chloride, 3-chloropropyltrimethoxysilane, 3-chloropropylsilanetriol, 3-aminopropyltriethoxysilane, 3-aminopropylsilanetriol, homopolymers thereof, and mixtures thereof.

BRIEF DESCRIPTION OF THE DRAWING

The subject matter of the present disclosure is pointed out with particularity, and claimed distinctly in the concluding portion of the specification. A more complete understanding of the present disclosure, however, may best be obtained by referring to the detailed description and claims when considered in connection with the following drawing FIGURE:

FIG. 1 illustrates an embodiment of an artificial turf treatment apparatus in accordance with the present disclosure.

DETAILED DESCRIPTION

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, systems and methods for the treatment of artificial turf are provided. A system may comprise any one of a cleaner, water, sanitizer/disinfectant or residual sanitizing coating composition, along with a suitable sprayer for applying same, such as an agricultural sprayer, to apply any combination of these solutions to the artificial turf. A system may comprise both an artificial turf treatment apparatus designed make application of chemicals to artificial turf more efficient, and a method of treating artificial turf using the artificial turf treatment apparatus.

In various embodiments of the present disclosure, a method of preventing transfer of pathogens between individuals interacting on artificial turf is provided. The method of preventing transfer of pathogens between individuals interacting on artificial turf comprises treatment of the artificial turf with an antimicrobial composition.

Definitions and Interpretations

As used herein, the term "artificial turf" broadly refers to a synthetic surface made to look like real grass, such as resembling a neatly trimmed lawn or grass playing field. The term "artificial turf" is broadly used to include all types and variations of artificial grass, from the simplest construction comprising only plastic fibers made to look like blades of grass bonded into a base material, to the more complicated constructions comprising plastic fibers made to look like blades of grass tufted in a base material, with at least one infill material distributed in the interstices between the plastic fibers. Artificial turf varies in quality and construction to address different uses and costs. For example, artificial turf used in a residential backyard as a small golf putting green may be very basic, just green colored plastic fibers glued into a base material. Artificial turf used on the field of a football stadium, however, is decidedly more complicated and expensive, and is typically cushioned to reduce player injury. Cushioning is often achieved by including various infill materials between the synthetic blades of grass. For example, a type of artificial turf used in professional sports may comprise filaments of plastic grass blades tufted or otherwise bonded into a plastic backing material, with multiple infill materials such as silica sand, cryogenic rubber and rubber particles (e.g., crumb rubber) packed into the interstices between the plastic blades of grass. In some examples, infill material comprises a bottom layer of sand, a middle layer of a mixture of sand and cryogenic rubber, and an upper layer comprising only crumb rubber. An exemplary artificial turf having infill materials and for treatment by the systems and methods herein is FieldTurf® brand of artificial turf available from Tarkett Sports, a division of the Tarkett Group. Heretofore, there are no clear methods to treat infill material with an antimicrobial composition because the infill material is lodged between the synthetic grass fibers in these types of cushioned turf.

The materials used in artificial turf vary widely, but are generally synthetic polymers. Thus, the synthetic blades of grass in artificial turf may comprise, for example, any combination of polymers such as polyethylene, polypropylene, polybutylene, polyethylene terephthalate, polyvinylchloride, polycarbonate, polyester, polyurethane, polystyrene, nylon, polytetrafluoroethylene, and so forth. The backing material can be a flat piece of flexible material, multiple yards in length and width yet relatively thin, such as from about ¼ inch to about 1 inch, comprising either a rubber material or any combination of the above-mentioned synthetic polymers, or a laminate composite. The infill materials, when present, may comprise any combination of sand and rubber particles. The sand may be ordinary silica play sand, such as seen in a child's sandbox, and may be of sufficient mesh size so that the sand particles fall into the artificial turf to a particular desired depth. The rubber particles may be synthetic or natural rubber, and may comprise chopped-up recycled tires, (a product referred to as "crumb rubber"). Rubber types include, but are not limited to, polyisoprene, styrene-butadiene copolymer, polybutadiene, acrylonitrile-butadiene copolymer, isobutylene-isoprene copolymer, ethylene-propylene monomer-ethylene propylene-diene monomer, polychloroprene, polysulfide, polydimethylsiloxide, fluoroelastomeric rubber, polyacrylate elastomeric rubber, and so forth. Infill material may also comprise cryogenic rubber, which refers to recycled and ground tire rubber from the "cryogenic method" in which vulcanized tire rubber is chilled to a temperature at which the rubber is brittle and then powdered while brittle under high-shear conditions. In this way, cryogenic rubber will tend to have a smaller particle size than crumb rubber, the latter of which is just recycled rubber chopped up into small pellets or a fine particulate.

As used herein, the phrase "treating an artificial turf" means to expose at least a portion of at least one of the components of an artificial turf to a chemical composition, including water, and/or to a surface-energy modifying process. Thus, the phrase is meant to include chemically coating individual plastic blades of grass, the underlying base material to which the blades of grass are attached, and/or any portion of any one or more infill materials, such as sand, cryogenic rubber, and/or crumb rubber. In various embodiments, treating an artificial turf comprises spraying or otherwise applying any combination of cleaners, water rinses, sanitizers and disinfectants to one or more components of the artificial turf. In various embodiments, treating an artificial turf comprises only spraying an antimicrobial composition on the plastic blades of grass. In other embodiments, treating an artificial turf comprises an agitation of the artificial turf, such that infill material is propelled out from the artificial turf. Treating an artificial turf may comprise a chemical treatment of the liberated infill particles while they remain temporarily in the air above the surface of the artificial blades of grass. The treatment of artificial turf may be referred to as both "onto and into" artificial turf. These phrases are used to indicate that treatment may superficially coat accessible surfaces, such as the tops of the synthetic blades of grass, and/or also coat surfaces down into the recesses of the artificial turf, such as the lower portions of the synthetic blades of grass at or near the attachment points to the base material, infill material near the upper portions of the turf not shielded by artificial blades of grass, or infill material in the air having been liberated out from the recesses of the turf by agitation. In some examples, it may be desirably to just treat the plastic blades of grass in artificial turf. In some instances, it may be desirable to just treat infill material as it is agitated out from the surface of the turf. In other instances, it may be desirable to treat both the synthetic blades of grass and the infill material, such as by agitating the turf to liberate the infill particles into the air and to spray both the plastic blades of grass and the suspended infill material using multiple sprayer nozzles aimed at different directions such as to target both the turf below and the infill particles in the air above the turf. Strategically placed sprayer nozzles can be directed vertically down, such to spray the top surface of the turf, and/or laterally out, parallel to the turf or at a greater angle, such as to spray the particles in the air above the turf.

As used herein, the actions "liberating infill material" or "liberating infill particles" refer to the act of moving particulate infill material physically out of the recesses of the artificial turf and into the air space above the turf. As mentioned, cushioned turf generally comprises at least some type of infill material down in the spaces between synthetic blades of grass. Liberating means to move those particles of infill material to at least some distance above the tips of the synthetic blades of grass. In various embodiments, liberating infill material means to get particles at least ¼ inch above the tips of the blades of grass. Liberating may comprise moving particles of infill material from between about ¼ inch to about 1 foot or more above the top of the turf surface. In various embodiments, an agitating module of an artificial turf treatment apparatus is designed to liberate infill material from artificial turf either by physically blowing it out or by contacting the particles of infill material and/or the plastic blades of grass trapping the particles, with moving bristles and/or rake tines to propel the particles out from the turf and into the air above.

As used herein, the term "electrostatic spraying" refers to the process of liquid chemical spraying wherein liquid spray leaving a spray nozzle is given a positive charge such that the positively charged droplets are attracted to negatively charged surfaces, including most environmental surfaces even when not purposely charged. Electrostatic spraying usually provides smaller droplet sizes than conventional pressure spraying through atomizing orifices. An electrostatic sprayer may include branched tubing and multiple spray nozzles such that only one voltage source is needed to apply a charge through the metal tubing and to each nozzle conductively connected via metal tubing. Electrostatic sprayers are available from Electrostatic Spraying Systems, Inc., (ESS), of Watkinsville, Ga. Commercially available sprayers can be modified if needed to accommodate multiple spray outlets.

As used herein, the term "pathogen" takes on the ordinary and customary meaning of a microorganism that causes infection in a host. Within the scope of the term, pathogens of interest include those that cause human infections, and these generally comprise bacteria, viruses and fungi. Further, pathogens recognized as microorganisms that transfer indirectly through contaminated surfaces, such as contaminated artificial turf, are of interest within the scope of the disclosure. For example, pathogens include, but are not limited to, hepatitis B virus, hepatitis C virus, human immunodeficiency virus (HIV), norovirus, poliovirus, rotavirus, influenza virus, adenovirus, *Staphylococcus aureus*, methicillin resistant *Staphylococcus aureus* (MRSA), vancomycin resistant *Enterococcus* (VRE), carbapenem resistant Enterobacteriacea (CRE), *Listeria* spp., *Klebsiella* spp., *Pseudomonas aeruginosa*, *Acinetobacter* ssp., *Bacillus anthraces*, *Salmonella* spp., *Campylobacter* spp., *Mycobacterium* spp., *Streptococcus* spp., *Clostridium difficile*, *Herpes gladiatorum*, *Herpes rugbiorum*, *Tinea pedis*, and *Tinea cruris*. Any one or more of these microorganisms, along with others now known or yet to be identified, may be responsible for infections spread between players interacting on an artificial turf playing field, and thus controlling growth and viability of these and other microorganisms on an artificial turf playing field by the systems and methods disclosed herein is a way to control infection between players on the field.

As used herein, the microbiology term "colony forming units" (CFU) refers to individual colonies of microorganisms counted on an agar plate. CFU is a measure of the level of contamination of a surface, whereby an agar plate is inoculated with a dilution of the microorganisms obtained from a test swab previously wiped on the surface to be tested. If the microorganisms are efficiently distributed on the agar plate, it can be generally assumed that each cell will give rise to a single colony, which can be counted. The counting of CFU's on an agar plate may be manual (e.g. assisted by a click-counter so as not to lose count), or may be electronic, such as by electrical resistance, flow cytometry, image analysis, or other method. Electronic methods for counting CFU's may be calibrated by hand counting. The appearance of each colony, (e.g. shape, color), can be indicative of the species of microorganism growing on the plate. Otherwise, a separate generic test can be used to verify the identity of a pathogen.

As used herein, the term "antimicrobial" is used generally to indicate at least some level of microbial kill by a composition or a coating on a surface of artificial turf. In other words, antimicrobial may refer to a liquid or gaseous contact sanitizer, disinfectant, or sterilant, or a residual antimicrobial coating that provides extended antimicrobial efficacy on a coated surface. For example, the term antimicrobial may be used to indicate a sanitizing level (3-log, or 99.9%) reduction in at least one organism, or a disinfection level (5-log, or 99.999%) reduction in at least one organism, or sterilization level reduction (no detectable organisms). Microorganisms may include any species of bacteria, virus, mold, yeast, fungi, or spore.

As used herein, the term "cleaner" takes on the common meaning of a composition that helps to remove grease and particular soils from surfaces. Such compositions may be soap-based, i.e., salts of fats, synthetic, or combinations thereof. Various non-limiting examples include detergent compositions based on any combination of anionic, nonionic, cationic and amphoteric surfactants, wherein anionic includes both synthetic anionic surfactants (e.g., sodium lauryl sulfate) and natural fatty soaps (e.g., coconut fatty acid-sodium salt).

As used herein, the term "rinse" takes on the common meaning of a water treatment to remove soils or cleaners from a surface. A water rinse may comprise distilled or reverse osmosis water, chemically treated water, any type of conditioned water, ordinary potable water, well water, municipal water, or water with an additive in it, such as a nonionic surfactant rinse aid.

As used herein, the term "sanitizer" or "disinfectant" refers to liquid or gaseous compositions providing at least some level of contact sanitization or disinfection. Sanitizer and disinfectant compositions for use herein include, but are not limited to, acid/anionic, peracetic acid, hydrogen peroxide, quaternary ammonium solutions (i.e., "quats"), chlorhexidine, triclosan, bromine, iodine, silver nitrate, elemental silver, mercuric chloride, glutaraldehyde, formaldehyde, phenol and derivatives thereof, ethanol, i-propyl alcohol, ozone, chlorine dioxide (gaseous and aqueous solution of chlorite), and hypochlorite (i.e., chlorine bleach), and combinations thereof where chemically compatible.

The terms "residual antimicrobial," "residual self-sanitizing," and "self-decontaminating surface" are used interchangeably to indicate a hard inanimate environmental surface, such as any of the components of artificial turf, which maintains antimicrobial efficacy over a certain period of time under certain conditions once the surface is coated with an antimicrobial coating composition. A coated surface may maintain residual antimicrobial efficacy indefinitely, or the coating may eventually "wear out" and lose its residual antimicrobial efficacy. An antimicrobial coating composition may function as a contact sanitizer, disinfectant, or sterilant when first applied to a surface, and also have the ability to leave behind a residual antimicrobial coating on the surface once dried or cured thereon that can keep inactivating new microorganisms that contact the coated surface. In various embodiments, coating compositions may not be antimicrobial until dried or cured on an artificial turf surface, but are still referred to as antimicrobial coating compositions because of their ability to produce a residual antimicrobial effect on the artificial turf surface. Antimicrobial coating compositions for use herein may provide a residual antimicrobial efficacy to a surface within artificial turf, meaning that a microorganism that comes in contact with the coated surface of the artificial turf may experience cell death, destruction, or inactivation. The residual antimicrobial effect made possible by the antimicrobial coatings is not limited by a particular mechanism of action, and no such theories are proffered. For example, an antimicrobial effect measured on an artificial turf surface may be the result of intracellular mutations, inhibition of certain cellular processes, rupture of a cell wall, immobilization and thus prevention of transfer or detection when swabbing, or a nondescript inactivation of the organism. Other antimicrobial effects may include inhibiting the reproduction of an organism or inhibiting the organism's ability to accumulate into biofilms. In other embodiments, an antimicrobial effect may be a stasis such that organisms cannot proliferate to the point of reaching a pathogenic level on the treated artificial turf surface.

As used herein, the term "antimicrobial coating composition" or "residual self-sanitizing coating composition" refers to a chemical composition comprising at least one chemical species, which is used to produce a residual self-sanitizing antimicrobial coating on an artificial turf surface after the composition is applied and then allowed to dry. However, the term is extended to include a composition that may be applied sequentially (e.g. over or under) or contemporaneously with the application of an antimicrobial coating composition comprising an antimicrobial active, such as to assist in bonding the residual antimicrobial coating to the surface, improve durability of the overall coating, and/or to provide a catalytic effect or some sort of potentiation or synergy with the residual antimicrobial coating comprising an antimicrobial active. For simplicity, each one of multiple compositions used sequentially or contemporaneously to produce an overall residual antimicrobial coating on an artificial turf surface is referred to as an "antimicrobial coating composition," even if one or more of the compositions used for coating has no identifiable antimicrobial active or where the active agent is uncertain. An antimicrobial coating composition may comprise a neat, 100% active chemical species or may be a solution or suspension of a single chemical species in a solvent. In other embodiments, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In various embodiments, chemical constituents within an antimicrobial coating composition may chemically react on the surface that the composition is applied to, such as while the composition is drying and concentrating on the surface. Antimicrobial coating compositions for use in various embodiments may further comprise any number and combination of inert excipients, such as for example, solvents, surfactants, emulsifiers, stabilizers, thickeners, free-radical initiators, catalysts, etc. Exemplary antimicrobial coating compositions that leave behind a residual self-sanitizing coating on an artificial turf surface, and that are suitable for use herein, include for example: a quaternary ammonium biocide-polymer complex exemplified in U.S. Pat. Nos. 6,017,561; 6,080,387; 6,270,754; and 6,482,392 assigned to The Clorox Company and incorporated herein by reference in their entireties; solutions of 3-(trimethoxysilyl) propyl dimethyl octadecyl ammonium chloride (CAS No. 27668-52-6, obtained under various trade names); SilverShield®, a coating that delivers antimicrobial silver over time and is available from Microban®, Huntersville, N.C.; and solutions and methods comprising various organosilanes, organic amines, titanium(IV) species, titanium sols, α- or β-hydroxyacid/titanium complexes, and combinations thereof, as exemplified in at least PCT International Patent Application Serial Nos. PCT/US13/073878; PCT/US15/059080; and PCT/US16/017599 assigned to Allied Bioscience, Inc. and incorporated herein by reference in their entireties; and in U.S. Pat. Nos. 10,040,952; 10,040,097; 9,963,596; 9,918,475; 9,856,360; 9,855,584; 9,757,769; and 9,528,009, each assigned to Allied Bioscience, Inc. and incorporated herein by reference in their entireties. In various embodiments, an artificial turf treatment apparatus is used to coat at least one component of the artificial turf with any combination of: (a) 3-(trimethoxysilyl) propyl dimethyl octadecyl ammonium chloride; (b) 3-chloropropyltrimethoxysilane; or (c) 3-aminopropyltriethoxysilane, or any of the corresponding alkoxides, silanol hydrolysis products, or homopolymers of these organosilanes. In various embodiments, a residual antimicrobial coating composition comprises one or any combination of these silanes along with an organic amine, such as triethanolamine. An organosilane coating applied to artificial turf may then be coated overtop with a titanium species, such as an aqueous mixture of $TiO_2$ or a titanium-sol that provides a thin film of $TiO_2$. In various embodiments, a second coating step of a titanium species acts to "seal" a prior organosilane coating onto a surface, thus extending durability. In other embodiments, an artificial turf surface is first coated with a titanium species and then with one or more of the silanes (a), (b), or (c), or simultaneously coated with an organosilane and a titanium species. In other embodiments, any other residual self-sanitizing coating, whether modifications of these quaternary or organosilane technologies, or comprising any other coating technology, are suitable for use in infection control on an artificial turf playing field as per the present disclosure.

As used herein, the term "organosilane" refers to silicon-containing organic chemicals, as opposed to inorganic forms of silicon, such as $SiO_2$ and water glass species ($Na_2SiO_3$, and the like). An organosilane is typically a molecule including carbon and silicon atoms, but may also include any other heteroatoms such as oxygen, nitrogen, or sulfur. Organosilane compounds for use in various embodiments herein may be chemically reactive or inert, and may be monomeric, dimeric, trimeric, tetrameric, or polymeric. Organosilane monomers for use in various embodiments may be chemically reactive in that they at least partially hydrolyze or self-polymerize, or form various adducts and/or polymers with other chemical species in a composition or on a surface of the artificial turf. Exemplary organosilanes for use in various embodiments include, but are not limited to, organosilanes having three reactive groups bonded to silicon and one non-hydrolyzable group bonded to silicon. Such organosilanes for use herein include, but are not limited to, 3-(trimethoxysilyl) propyl dimethyl octadecyl ammonium chloride, 3-chloropropyltrimethoxysilane, and 3-aminopropyltriethoxysilane, and any of their corresponding adducts (e.g., with a titanium species), any of their corresponding hydrolysis products (e.g., silane triols), and any of their self-condensation products (e.g., homopolymers with any chain length distribution).

As used herein, the term "titanium species" refers to any chemical compound comprising at least one tetravalent titanium atom, regardless if monomeric, dimeric, trimeric, or polymeric. Non-limiting examples include titanium (IV) oxide ($TiO_2$) in any form, other Ti(IV) species, (e.g., $TiCl_4$, Ti—(O-i-$C_3H_7$)$_4$ and any other Ti(IV) alkoxide, phenoxide or halide). Various forms of $TiO_2$ for use herein include, but are not limited to, rutile, anatase, brookite, hollandite-like, ramsdellite-like, α-$PbO_2$-like, baddeleyite-like form, orthorhombic $TiO_2$—OI, cubic, and/or cotunnite-like forms. The most common crystalline forms are anatase, brookite and rutile. In various examples, a Ti(IV) species for use herein comprises an aqueous colloid of $TiO_2$ or a suspension of Ti nanoparticles. Further, Ti(IV) species for use herein include "titanyl-oxide moieties," which is a broad term used herein referring to any and all Ti compounds and mixtures known to form $TiO_2$ thin films, or at least suspected as able to form $TiO_2$ thin films, such as via the sol-gel process. A titanyl sol-gel is a precursor in the preparation of $TiO_2$ thin films. For example, a mixture of Ti($OC_4H_9$)$_4$, ethanol, water, and diethanolamine, in a 1:26.5:1:1 molar ratio, has been disclosed as forming a $TiO_2$ film (see J. Yu, et al., *Materials Chemistry and Physics*, vol. 69, pp 25-29 (2001)). This reference further discloses that whether or not the film is photocatalytic depends, inter alia, on the curing conditions for the sol-gel after surface application, e.g. using high temperatures. In another non-limiting example, a sol-gel route to mesoporous and nanocrystalline anatase thin layers begins with acidic hydrolysis of titanium isopropoxide, (see F. Bosc, *Chem. Mater.*, 15(12), pp 2463-2468, (2003)). In various examples herein, titanyl-oxide moieties, such as a Ti-sol gel, provides a sealing coating to extend the durability of an antimicrobial coating underneath.

In certain examples, titanyl-oxide moieties for use herein comprise a colloidal suspension of from about 0.5 wt. % to about 50 wt. % $TiO_2$ in water. In other examples, titanyl-oxide moieties comprise an aqueous mixture of Ti—(O-i-$C_3H_7$)$_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—(O-i-$C_3H_7$)$_4$ or $TiCl_4$. A $TiO_2$ sol-gel composition, when coated onto a portion of a surface, provides a thin film $TiO_2$ coating on the portion of the surface, and may be applied overtop or underneath another coating on the surface.

In various embodiments, titanyl-oxide moieties comprise $Ti(OR^3)_4$, wherein $R^3$ is alkyl, substituted alkyl, aryl, or substituted aryl, and wherein the four separate $R^3$ groups are identical or different. Examples of $Ti(OR^3)_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-$C_3H_7$)$_4$) or dissolved in an alcohol or other organic solvent(s), such as the corresponding alcohol, where feasible, (methanol, ethanol, i-propanol, etc.). Thus, titanyl-oxide moieties may in some instances comprise a solution of Ti—(O-i-$C_3H_7$)$_4$ in isopropanol or some other alcohol.

In various embodiments, titanyl-oxide moieties comprise $Ti(OR^3)_4$, wherein $R^3$ is alkyl, substituted alkyl, aryl, or substituted aryl. In certain aspects, titanyl-oxide moieties may further comprise a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, titanyl-oxide moieties consist essentially of Ti—(O-i-$C_3H_7$)$_4$. Other examples include Ti—(O-i-$C_3H_7$)$_4$ and an alcohol, and a composition comprising Ti—(O-i-$C_3H_7$)$_4$ and isopropanol.

In various examples, titanyl-oxide moieties for use herein comprise an aqueous solution of peroxotitanium acid and peroxo-modified anatase sol, which is disclosed in the literature as a room temperature route to $TiO_2$ thin films, (see Ichinose, H., et al., *Journal of Sol-Gel Science and Technology*, September 2001, Volume 22, Issue 1-2, pp 33-40, and Ichinose, H., et al., *J. Ceramic Soc. Japan*, Volume 104, Issue 8, pp 715-718 (1996)).

In various examples, the titanyl-oxide moieties for use herein is a sol-gel that comprises about 0.5 wt. % peroxotitanium acid and about 0.5 wt. % peroxo-modified anatase sol, remainder water. A non-limiting example of a titanyl-oxide moieties composition for use herein comprises 0.85 wt. % of a mixture of peroxotitanium acid and peroxo-modified anatase sol (titanium oxide (IV)), remainder water. In various examples, a titanyl-oxides moieties composition comprises 0.8-0.9 wt. % of a mixture of titanium oxide (IV) and peroxotitanium acid, with the remainder, i.e., 99.1-99.2 wt. %, water. In various embodiments, this sol-gel mixture may be referred to as "0.85 wt. % aqueous peroxotitanium acid and peroxo-modified anatase sol."

Titanium (IV) species for use in various artificial turf treating and coating processes may be white or transparent, and may be photocatalytic or not. A titanium (IV) species, including the group of titanyl-oxide moieties discussed above, may be cast onto artificial turf surfaces to produce an antimicrobial coating, or used as a bonding agent or sealant to bond other substances, such as organosilanes, to artificial turf surfaces to form more durable antimicrobial coatings on the turf surfaces.

Artificial Turf Treatment Apparatus

An artificial turf treatment apparatus in accordance to the present disclosure comprises both an agitating module and a spraying module. The apparatus may further comprise a hitch, such that the apparatus can be towed or attached to the front of a vehicle for pushing, and optionally a surface energy treatment module, such as an ozone generator or a corona discharge generator. An apparatus may take on the physical appearance of a flat hauling trailer, an agricultural till, and/or a tow-behind or push-in-front sweeper in both approximate size and shape. An apparatus may be generally flat, such as 0.5 feet to about 2 feet in height, as per these familiar pieces of equipment, several few feet to about 8 feet in length from hitch to backend, and from about 3 feet to about 15 feet or more in width. The width of an apparatus may be designed to accommodate certain treatment jobs. For example, an apparatus useful for treating all of the artificial turf laid down in a football field in an NFL stadium may be at least 3 feet wide, at least 10 feet wide, at least 15 feet wide, at least 20 feet wide, or at least 25 feet wide, so that a reasonably finite number of passes by the apparatus over the artificial turf field will eventually treat the entire field. The width of an apparatus is unlimited, and can even be as wide as agricultural watering systems. The width of an apparatus may also be designed with the method of mobilizing the apparatus in mind, such as if the apparatus is to be towed behind a small tractor or other motorized or electrical vehicle, or pushed by a vehicle. It is important to understand that an artificial turf treatment apparatus may be designed as an attachment for the front of a vehicle rather than as equipment that is towed behind a vehicle.

A. Agitating Module:

In various embodiments, an artificial turf treatment apparatus comprises an agitating module. An agitating module comprises any number of physical devices, stationary or moving, capable of disturbing a sample of artificial turf, and in some instances, capable of agitating infill material out from the recesses of the artificial turf. In some cases, the agitating module may comprise air jets that force air down into the turf to mobilize the infill material, by simply blowing the particles out. In other cases, the agitating module comprises a broom, a rake, or related components thereof, such as bristles and/or tines, in any combination, capable of physically impinging upon particles of infill material to physically propel the particles out from the turf. In various embodiments, bristles and/or tines may be stationary or movable, and in the latter, may be movable on a rotating cylinder. In various embodiments, bristles and/or tines may impinge on a synthetic blade of grass and that movement of the plastic grass blades may in turn propel particles of infill material out from the turf. In other embodiments, artificial turf may be devoid of infill material, and the agitating module is thus designed to just splay apart synthetic grass blades as the apparatus is pulled over the turf, such as to expose more of the length of the blades of grass and even the base material for treatment.

In various embodiments, an agitating module comprises a long rectangular broom, such as measuring from about 3 feet to about 25 feet in width, but similar in general appearance to a consumer or institutional cleaning broom, i.e., about 0.5 feet in both height and length. The broom may comprise any number of rows of bristles of any size, and one or more rows of bristles may be removed to accommodate one or more rows of spray nozzles in the base of the broom. In various examples, the agitating module comprises rake tines of any dimension, such as 0.5 feet long and about 1 inch in height and width. An agitating module may resemble a very wide consumer retail leaf or lawn rake, familiar to homeowners, but with much greater width.

In various embodiments, an agitating module resembles a commercial artificial turf broom. An example is the Verti-Broom® available from Redexim North America, Valley Park, Mo. The Verti-Broom® comprises a triangular arrangement of stationary bristles for sweeping artificial turf.

In various embodiments, an agitating module resembles a tow-behind street broom, which comprises a large cylindrically shaped, rotating broom. An example of such a rotating broom is the Model 53H or Model 53T Tow-Behind Broom available from M-B Corporation, Chilton, Wis. In Model 53H, the rotating broom is hydraulic, whereas in the Model 53T the rotating broom is self powered by movement of a set of wheels through a gear system.

As described in more detail below, an artificial turf treatment apparatus also comprises a spraying module. One embodiment of an artificial turf treatment apparatus comprises the Model 53T Tow-Behind Broom, or the Verti-Broom®, or a similar commercial sweeping piece of equipment, further equipped with liquid tanks and sprayer nozzles positioned in front of, behind of, and/or between the bristles, to spray the artificial blades of grass and the turf infill particles with an antimicrobial composition as the tow-behind apparatus is moved along a section of artificial turf.

In various embodiments, an agitating module resembles an agricultural till or a tow-behind rake that is dragged behind a tractor to rake the artificial turf and liberate the infill particles. A non-limiting example of a tow-behind rake that is usable as the agitating module and adaptable to an artificial turf treatment apparatus includes the Verti-Rake® from Redexim North America, Valley Park, Mo. For combinations of bristles and tines in an agitating module for use herein, a frame, such as the SISIS® Towed Implement Frame, available from SISIS® USA Turf Equipment and distributed by CS Trading, LLC, Liberty, S.C., provides a steel framing onto which sweeping and raking implements can be attached, in any combination, along with attachment of a spraying module. An exemplary ready-made combination broom and rake for artificial turf maintenance is the ASR2® Artificial Surface Grooming Rake available from SCH Supplies, LTD, UK. The ASR2® Artificial Surface Grooming Rake is readily adapted into a complete artificial turf treatment apparatus in accordance with the present disclosure by attaching a spraying module onto the frame of the ASR2® and directing various spray nozzles into the desired directions.

Various embodiments of an artificial turf treatment apparatus may further comprise wheels, such that the depth of the bristles and/or tines of the agitating module can be modulated by the size and compressibility of the wheels, or to power rotating bristles or tines. In other words, the artificial turf treatment apparatus may have its own set of wheels, like a flat trailer with a pair of wheels, to support the weight of the equipment associated with the apparatus, and/or to power other elements such as rotating bristles or tines, or sprayers.

In various embodiments, the depth of penetration of the bristles and/or tines of the agitating module into the artificial turf may also depend on the overall weight of the apparatus. For example, the agitating module or other portion of the overall apparatus may be weighted such that a particular depth of the bristles and/or tines is achieved. Other variables may be adjusted, such as the size and ballast of a set of wheels, resiliency of plastic or metal bristles and/or tines, size of the bristles and/or tines, the ability to raise/lower the entire apparatus hydraulically, and so forth. The desired depth of the bristles and/or tines of the agitating module into the turf may depend on which infill material is to be liberated from the interstices of the turf. For example, a shallow depth may be targeted if just the crumb rubber is to be liberated from the turf. Correspondingly, a deeper depth may be targeted if the method of treating the artificial turf is to include liberated cryogenic rubber particles and/or sand from the artificial turf.

In various embodiments, components of the agitating module, such as a row of bristles, a rotating drum of bristles, or a row of rake tines, may be height adjustable with any type of mechanism. For example, bolts that hold a broom onto a frame of the apparatus may be loosened and the broom moved in height relative to the surface of the turf, and then the bolts retightened. In some instances, height may be more easily adjusted, such as with a knob or a lever. In this way, various components can be raised or lowered relative to the surface of the turf so that the desired depth of the bristles and/or tines into the turf is achieved. The ability to adjust height can be used to compensate for the changing weight of the overall apparatus as chemical composition is dispensed from one or more tanks on the apparatus. As the apparatus becomes lighter during use due to dispensation of liquid composition, the wheels of the apparatus may become less compressed, and the entire apparatus may rise in height during use. To compensate, components of the agitating module can be lowered.

B. Spraying Module:

In various embodiments, the spraying module comprises at least one tank (i.e., a liquid reservoir) and all the spray components necessary for any one of manual spraying, compressed air spraying, or electrostatic spraying of chemicals residing in the tank out to the artificial turf, including spraying down in the blades of grass, onto the base material, and/or onto any liberated particles of infill materials that may also be targeted for treatment.

In various embodiments, the spraying module comprises one, two, three, four or more tanks, each suitable for liquid storage and, in particular, for the storage of one or more residual self-sanitizing coating compositions that may comprise solvents and chemicals that attach or otherwise bond to the various materials of artificial turf. A tank may be fashioned of any suitable material that is able to contain liquids and that is chemically compatible with the compositions contained therein, such as plastic, glass, or metal, and may further comprise a removable closure for refilling purposes. In various embodiments, a tank may comprise a bag-in-a-box package, or a standard pail with a bung that can be tapped. Plastic tanks associated with agricultural spraying are especially suited. A tank may be of any capacity, such as for example, from about 0.5 liter capacity up to about 200 liters (i.e., approximately the size of a 55 gal drum). The desired capacity of a tank may depend on a number of considerations, such as, how many tanks are included for an embodiment of the artificial turf treatment apparatus, the nature of the liquid materials in the tank, (e.g. as relating to the amount of material desired on a surface of artificial turf), whether the tank is refillable or not, the overall weight of the apparatus, and how the apparatus will be moved over artificial turf (pushed or pulled), amongst other considerations. For example, an artificial turf treatment apparatus may comprise a spraying module having only one 90 liter tank, whereas another artificial turf treatment apparatus may comprise a tank module comprising three 30 liter tanks, e.g. for application of multiple compositions sequentially or simultaneously. In various embodiments, an individual tank further comprises at least one of a weight sensor, a liquid level float, and an optical sensor to monitor changes in weight of the tank or changes in the liquid level line inside the tank.

Exemplary spray modules minimally comprise a tank as described above, a fluidic pump, a chemical delivery tube suitable for liquid flow, an on/off control e.g. an electrical switch or fluid valve, and a spray nozzle in fluid communication with the tank. Depending on the desired mode of spraying enabled by the spraying module of the apparatus, only a chemical delivery tube may be connected to a spray nozzle. In other examples, both a chemical delivery tube and a compressed air supply line may be connected to a spray nozzle. In general, an electrostatic spray system, although including both of these, does not require a third line to the spray nozzle, i.e. an electrical cable, because an electrostatic spray system generally comprises an internal turbine operated by the compressed air, and this turbine produces the electricity supplied to the electrode needle of the spray orifice to charge the aerosolized particles. In various embodiments, compressed air may be supplied by a gas-powered or electrically-powered air compressor placed onboard the artificial turf treatment apparatus.

Regardless of what type of spraying the spraying module comprises, various on/off sensors and switches, weight sensors, liquid level floats, optical sensors, and the like, may be employed to enable recordation of chemical spray times and/or the amount of material dispensed from a tank during an artificial turf treatment session. These data may be sent wirelessly to a remote computer or recorded with an onboard computer such as a tablet. For example, a decrease in weight in a tank of chemicals can be measured while another sensor records the duration the spraying module is actuated in spraying the chemicals onto the turf. Then the amount/time, such as grams/sec of spray application can be calculated. In various embodiments, and depending on the particular antimicrobial compositions used to treat artificial turf, the type of spraying, and other considerations, the coating of a surface of a component of artificial turf may be from about 1 µg/cm$^2$ up to about 500 mg/cm$^2$ of turf surface, after surfaces are allowed to dry. For example, artificial blades of grass and particulate infill material may be coated with from about 1 µg/cm$^2$ up to about 500 mg/cm$^2$ of composition, based on the dried weight per unit area. Components that may enable each of these modes of spraying are available, for example, from Finishing Consultants, Inc., Everett, Wash., amongst other suppliers.

1. Manual Spraying:

In various embodiments, the spraying module usable for manual spraying comprises a fluidic pump that moves chemicals from one or more tanks through chemical delivery tubing out to a spray nozzle. The pump may comprise any type of in-line fluid pump that can supply the liquid to be sprayed at a suitable pressure such that the liquid is aerosolized by the spray nozzle, such as an electrical fluid transfer pump. In various embodiments, a spray module comprises two sections of chemical delivery tubing with connectors at each end of both sections, a spray nozzle, and an in-line fluidic pump disposed anywhere between the spray nozzle and the tank, wherein one section of hose fluidically connects a tank to the inlet of the fluid pump and the other section of hose fluidically connects the outlet of the fluid pump to the spray nozzle. The connectors may be of any type, such as for example, quick disconnect Swage-type fittings, or threaded connectors, or any other type of connectors for fastening hose to a hose bib. The chemical delivery hose may comprise any material that is reasonably flexible, such as plastic, and may comprise combinations of materials. For example, a chemical delivery hose may comprise a polyethylene tube surrounded by a stainless steel or other type of metal mesh for reinforcement. In this way, the metal mesh protects and reinforces the inner polyethylene tubing, extending its life. Other tubing can be selected depending on the corrosive nature of the chemicals to be sprayed, and include for example, polycarbonate and Teflon. The inside diameter of a chemical delivery hose is from about 0.25 inches up to about 2 inches.

2. Compressed Air Spraying:

In various embodiments of compressed air spraying, the spraying module may comprise a chemical delivery hose enabling fluid communication between a tank and a spray nozzle as per the manual spraying option. In various embodiments, compressed air spraying by the spraying module is equivalent to commercial liquid spraying seen in the painting and finishing industry wherein the tank of liquid is pressurized rather than pumped out. In compressed air spraying, pressure in the tank of liquid forces liquid from the tank through a delivery hose to the spray nozzle where it is atomized. In various embodiments, the spraying module further comprises an air compressor that pressurizes a tank in the tank module. A pressurized tank for liquid spraying is sometimes referred to as a "pressure pot." The air compressor may cycle on and off as necessary to maintain a constant pressure in the tank, such as up to about 100 psi. The air compressor may switch on automatically after a period of spraying that acted to reduce the pressure in the tank below a certain threshold pressure. While mobile in a field of artificial turf being treated, an onboard compressor may be powered by a small gas-powered engine, e.g. 0.5 to 2.5 hp.

It's important to note that chemical mixing can also be achieved by utilizing two or more tanks and configuring the spraying module to draw upon the two or more tanks at the same time and at a prescribed mixing ratio. A switchable valve may enable choosing one tank from two or more tanks present, or for choosing to draw liquid from two or more tanks at the same time. For example, a 3-way "T-valve" enables the choice between an "off position," connection between the spray nozzle and only a first tank, connection between the spray nozzle and only a second tank, or connection between the spray nozzle and both the first and second tanks. Various sized orifices may be placed in the valve or in the dip tubes extending into each tank such that a prescribed metering of chemicals out to the artificial turf is achieved, recognizing that the draw of liquid from each of two tanks may be configured to be different by placing different diameter orifices in each of the flow streams from the two tanks.

3. Electrostatic Spraying:

In various embodiments, the spraying module comprises an electrostatic spray system. Electrostatic spraying comprises positively charging the atomized liquid as it leaves the spray gun such that the atomized particles are attracted to a surface that is electrically grounded, e.g., artificial turf laid on soil, sand, concrete or asphalt having a natural earth ground. For the spraying modules, an electrostatic spray system comprises two connections, one comprising the chemical delivery hose and the other comprising the compressed air supply line to operate the charging turbines. The liquid chemicals to be sprayed may be supplied to the electrostatic spray nozzles by fluidic pumping (an in-line fluid pump, electrically or gas-engine powered) or from a pressurized tank pressurized by an onboard gas-powered air compressor.

In various embodiments, a spraying module may comprise a manifold directly fed from one or more tanks, further comprising multiple outlets such as a plurality of spray nozzles positioned along the manifold. In this way, a single manifold may be pressurized to produce a spray pattern from each one of a plurality of spray nozzles. In various embodiments, tubing lines may begin at the tank and then end in a spray nozzle positioned at the back of the apparatus such that spray can be directed off the back of the apparatus and onto and into the artificial turf. There may be a plurality of lines coming from a single tank, each one terminating in a spray nozzle. Each spray nozzle may be aimed in a particular direction such as to provide a spray pattern down into the turf and/or out laterally to particles of infill material liberated by the agitating module.

The spray nozzles for the spraying module may be chosen on the basis of sprayer type, i.e., pressure or electrostatic, and for their spray pattern, output volume, durability, compatibility with various liquid chemicals, and so forth. In various embodiments, an electrostatic sprayer is obtained from ESS Inc. and modified as necessary to accommodate a plurality of spray nozzles. Nozzles may be brass or stainless steel, or comprise any type of plastic. Spray nozzles for use herein are well-known in agriculture for spraying water, pesticides, and herbicides.

An embodiment of an artificial turf treatment apparatus 1 is illustrated in FIG. 1. It should be understood that this particular and very specific configuration of an artificial turf treatment apparatus in accordance to the present disclosure is not meant to be limiting in any way. Variations of this configuration, such as, for example, an apparatus having only brooms or only rakes, or having one or two spray bars rather than three, would also fall within the scope of the present disclosure.

As shown in FIG. 1, the artificial turf treatment apparatus 1 comprises a frame 2 onto which various components of the apparatus can be secured in particular locations, and with adjustability if desired. In various embodiments, components that are part of an agitating module, a spraying module, a hitch, and an optional surface energy treatment module, for example, may be bolted, welded or otherwise permanently or adjustably fastened to this structural frame 2. As discussed above, set of wheels 5 and hitch 3 may be included on the frame 2 for mobilizing the apparatus and supporting the weight. As shown, a small tractor 4 may be used to tow the apparatus over sections of artificial turf requiring treatment.

With continued reference to FIG. 1, the agitating module comprises a first rake 6, a second rake 7, and a broom 8. In this way, this particular embodiment utilizes a combination of stationary bristles and stationary tines as the agitating module for liberating particulate infill material out from the recesses of the artificial turf. As discussed, other agitating modules may be configured differently, such as having only a rotating drum of bristles as seen in some tow-behind street brooms or some other configuration of bristles and/or tines in any combination. The apparatus 1 illustrated further comprises a spraying module comprising a liquid storage tank 9, filled for example with a residual antimicrobial coating composition, a fluidic pump 10, and three spray bars, a first spray bar 11, a second spray bar 12 and a third spray bar 13. The first spray bar 11 comprises a plurality of spray nozzles 14, the second spray bar 12 comprises a plurality of spray nozzles 15, and the third spray bar 13 comprises a plurality of spray nozzles 16. Any number of spray bars may be attached to the frame 2, and any number of spray nozzles may be arranged down the length of a spray bar, such as for example, 1 nozzle per foot. In various applications, there may be 1 to about 6 nozzles per foot of width of the apparatus. As discussed, the number, position, spray pattern and direction that the spray nozzles point are variables that can be manipulated to ensure certain components of the artificial turf receive chemical treatment, e.g., the plastic blades of grass, the underlying base material, and/or the various infill materials when projected into the air.

For example, the first rake 6 may just splay apart the plastic blades of grass of the turf and the first spray bar 11 may have its nozzles 14 directed vertically straight down such that the antimicrobial liquid is sprayed down in between splayed apart blades of grass, impinging into the recesses of the grass and onto the base material below. The second spray bar 12 may have its nozzles 15 directed at an angle from vertical, out toward the rear of the apparatus to impinge spray on the particles of infill material that are jettisoned into the air from the action of the first rake 6 and second rake 7. For example, the nozzles may be aimed at from about 5° from vertical out to nearly horizontal (i.e., 90°), parallel to the plane of the turf. Further, the nozzles 16 on the third spray bar 13 may be aimed such that their spray is projected nearly horizontal, in order to spray particles of infill material jettisoned into the air from the action of the broom 8. Of course, all the nozzles along any one spray bar need not be aligned such that they all spray in the same direction. For example, every other nozzle may aim straight down while the other nozzles in the series are aimed at an angle from vertical.

As shown in FIG. 1, the tank 9 is connected to the fluidic pump 10, and the fluidic pump 10 is connected to the three spray bars, by appropriate lengths of tubing, e.g. copper tubing, capable of transferring fluid. In a simple configuration, the fluidic pump 10 is an electrical pump, which is powered by the electrical system of the tractor 4, be it the battery or, when running, the alternator or generator depending on the tractor's electrical system. The fluidic pump 10 may be electrically wired to the tractor by a harness crossing over the hitch 3 and out to the frame 2, including a switch in the tractor that the driver can operate to start and stop the fluidic pump 10 from running.

In operation, such as to treat a section of artificial turf to eliminate or reduce the spread of pathogens between players interacting on the artificial turf, the apparatus 1 is towed behind the tractor 4 wherein the two rakes and the broom splay apart the blades of artificial grass and jettison the particles of infill material into the air underneath and behind the frame of the apparatus. While the apparatus is in motion over the turf, the fluidic pump 10 is activated and running so as to pump residual antimicrobial coating composition from the tank 9 through the spray bars and out from the various nozzles such that the blades of plastic grass, the base material into which the grass is tufted, and the various infill materials are all coated with the residual antimicrobial coating composition. In treating artificial turf in this manner, the apparatus may be rolled over the same section of turf repeatedly, such as three passes, in order to thoroughly coat all components of the turf. Further, the apparatus may be towed over the turf without the pump 10 running, such as to redistribute the infill material into the recesses of the turf after the components of the turf are coated. So for example, the apparatus 1 may be pulled over the same section of turf a total of four times, the first three times with the pump running and spray coming out from all the nozzles, and the fourth time without the pump running to ensure the infill material is properly redistributed. Furthermore, repeated passing of the apparatus without the pump running is a method of drying the coating on the particles of infill material as they are jettisoned back into the air where they may dry faster. A first pass of the apparatus 1 over the artificial turf may be to provide surface energy modification of various portions of the artificial turf. For example, ozone or an ozone solution may be distributed out the same spray bars and nozzles in a first pass of the apparatus over the turf, prior to any treatment with a residual antimicrobial coating composition. After the process, the components of the artificial turf comprise a residual antimicrobial coating that reduces or eliminates pathogenic contamination of the turf and, consequently, transfer of pathogens between individuals.

C. Optional Surface Energy Treatment Module:

In various embodiments, an artificial turf treatment apparatus in accordance to the present disclosure further comprises a surface energy treatment module configured to reduce the surface energy of a surface of a component of the turf to a surface energy level lower than the surface energy level prior to the surface modification. As is well known in the field of plastics, most synthetic polymer surfaces are hydrophobic and resist wetting with aqueous compositions. In other words, a drop of aqueous composition placed on a plastic surface will have a high contact angle, meaning it will be beaded up rather than spread out thinly. Plastics known to be the worst for wetting include polyolefin plastics, such as polyethylene and polypropylene. In treating artificial turf with an aqueous antimicrobial coating composition, the various plastic surfaces, particularly the plastic blades of artificial grass, may not wet sufficiently such that the aqueous coating composition is distributed evenly on the entire surface of each blade of grass. Instead, the aqueous antimicrobial composition may just bead up on the plastic on the plastic blades of grass and dry in a spotted pattern, leaving untreated portions.

Surface modification is a known process by which the surface energy of a plastic is lowered. Although "lowered" is a relative term, any plastic surface will have a particular surface energy, and in the case of polyethylene and polypropylene, that surface energy is high, preventing aqueous wetting. Surface energy modification lowers the surface energy of a plastic surface to a level less than what the surface had before the surface energy modification. So although the absolute measure of the surface energy may not be known, it is well known that, at least relatively, surface energy modification lowers the surface energy of the plastic surface to an absolute level that is lower than the surface energy of the beginning, untreated surface. It is also known qualitatively that surface energy modification of a plastic surface changes the wettability of the surface, and that after surface energy treatment, a drop of water on the surface will have a lower contact angle and the water will spread more evenly across the surface.

Surface energy treatment processes involve modification of the surface of the plastic, and include such processes as ozone treatment, corona discharge, plasma treatment and acid etching. One of the more practical surface energy treatment methods for large areas of artificial turf is ozone treatment. Ozone is readily generated from the oxygen in air or from a direct oxygen feed by an electrical spark, and the ozone thus generated may be conducted through nozzles positioned close to or down below the surface of the artificial turf to treat the surfaces of the various materials present. Ozone has some solubility water, and a surface treatment module may be configured to produce an aqueous solution of ozone that is dispensed from the artificial turf treatment apparatus into the artificial turf, such as just after the aqueous ozone solution is freshly prepared.

In various embodiments, a surface energy treatment module for use herein comprises an ozone generator. In various embodiments, the module further comprises an oxygen tank to provide a pure oxygen feed into the ozone generator. In certain embodiments, the ozone generated from the ozone generator is bubbled into water to create an ozone solution, and then the aqueous ozone solution is distributed through components of the spraying module and onto the artificial turf, or through a separate sprayer system that includes a dedicated pump, tubing and spray nozzles as per the spraying module used for distributing the antimicrobial compositions. In one non-limiting configuration, the antimicrobial composition and the aqueous ozone solution can be fed from separate dedicated tanks through the same in-line fluidic pump and out to common spray nozzles by turning a valve to connect the fluidic pump to the appropriate tank.

Methods for Treating Artificial Turf, Methods of Applying a Chemical Composition to Infill Material Present in Artificial Turf, and Methods to Reduce or Eliminate the Transfer of Pathogens Between Individuals Interacting on Artificial Turf.

1. Conventional/Electrostatic Application of Cleaners, Rinses, Sanitizers, Disinfectants and Residual Antimicrobial Coating Compositions to Artificial Turf:

In various embodiments, a method of treating artificial turf comprises application of any combination of cleaners, rinses, sanitizers and disinfectants though a sprayer or other application device onto artificial turf in need of such treatment. For example, artificial turf may be washed by successive application of a cleaner and a rinse. These steps may be repeated as many times as necessary to provide artificial turf that is deemed substantially free of grease, grime, soils, and biological fluids. In some instances, drains are provided underneath artificial turf installations, and these drains provide a convenient exit for the soiled solutions, such that they don't pool up on the turf. In some examples, washing, rinsing and disinfection are provided in sequence to the turf, such as through an agricultural sprayer.

An agricultural sprayer for use herein may be a type of farm sprayer that is towed behind a tractor (i.e., a pull-type farm sprayer) or that is integral with a tractor (i.e., a self-propelled farm sprayer). Various farm sprayers, some having spray booms over 100 feet wide, are available from John Deere, Hagie, Hardi, Case IH, New Holland, AGCO, and Equipment Technologies, amongst other suppliers. These farm sprayers have large tanks for holding many gallons of liquid to be sprayed. In various aspects, one of these farm sprayers is used to treat sections of artificial turf with various chemical compositions.

In various embodiments, an electrostatic agricultural sprayer is used to apply various materials to artificial turf. In one non-limiting example, a self-contained narrow row electrostatic greenhouse sprayer from ESS, (Electrostatic Spraying Systems, Watkinsville, Ga.) is used to apply materials to artificial turf. Of particular use is the SGC Supercharged sprayer, which comprises 14-24 air-assisted electrostatic nozzles, a 30-gallon polyethylene tank, and a 21.5 HP on-board gasoline engine. This particular farm sprayer provides about a 40 µm droplet size from the sprayers, with minimum drift. As per spraying plants, this sprayer provides charged particles which attract to the surfaces of the components of artificial turf, much like to the under-the-leaf coating of foliage. This sprayer is compatible with most chemicals and is typically used with fungicides, making it ideal for spraying cleaners, sanitizers, disinfectants, and residual antimicrobial coating compositions onto artificial turf surfaces.

In various embodiments, the farm sprayer, such as the ESS sprayer above, is used to apply various chemical compositions and rinses to a section of artificial turf, such as by moving the sprayer across the field for as many passes as necessary to apply the desired number of chemicals across the desired sections of turf in need of treatment. In certain examples, the farm sprayer is used to apply detergent and subsequent water rinsing to the turf section. In other embodiments, washing and rinsing is followed by an application of a sanitizer or disinfectant, such as a peroxide-based, quaternary-based or chlorine-based product. In other examples, the farm sprayer is used to apply a residual antimicrobial coating composition to the turf. The application of residual antimicrobial coating may then be followed by application of a titanium species, such as to seal in the residual antimicrobial coating onto the surfaces of the turf. In this way, the farm sprayer, or any other sprayer such a conventional "Hudson" sprayer (a consumer/industrial home & garden/agricultural sprayer with a hand-pump to pressurize a tank, from the H.D. Hudson Manufacturing Co.), can be used to apply any combination of cleaners, rinses, sanitizers, disinfectants, residual antimicrobial coatings and titanium species to artificial turf. In various embodiments, the farm sprayer may be used onto to wash and rinse the turf in preparation for a more thorough application of a residual antimicrobial coating using a custom-designed artificial turf treatment apparatus as explained below.

2. Application of Cleaners, Rinses, Sanitizers, Disinfectants and Residual Antimicrobial Coating Compositions to Various Components of Artificial Turf Using a Customized Artificial Turf Treatment Apparatus:

In various embodiments, a method of applying a chemical composition to particles of infill material present in artificial turf comprises liberating the particles out from the artificial turf and spraying the particles while the particles are temporarily suspended in air above the artificial turf. In various embodiments, step of liberating the particles of infill material comprises the action of bristles or tines on the particles, the bristles or tines being part of an agitating module of an artificial turf treatment apparatus.

In various embodiments, a method to reduce or eliminate the transfer of pathogens between individuals interacting on artificial turf comprises treating the artificial turf with a residual antimicrobial coating composition. In various embodiments, the step of treating the artificial turf comprises moving an artificial turf treatment apparatus over the artificial turf at least one time, the artificial turf treatment apparatus comprising an agitating module, a spraying module, and optionally a surface energy treatment wherein the spraying module dispenses at least one antimicrobial composition onto and into the artificial turf. In various embodiments, the agitating module is configured with stationary and/or movable bristles and/or tines that propel particles of infill material into the air as the apparatus is moved over the turf, wherein the particles are sprayed with the antimicrobial composition. In certain examples, the spraying module further comprises at least one tank enclosing the antimicrobial composition dispensed onto the artificial turf. In some instances, the antimicrobial composition comprises a residual antimicrobial coating composition. The residual antimicrobial coating composition may comprise any combination of organosilane, titanium species, and organic amine.

In various embodiments, the step of moving the artificial turf treatment apparatus over the artificial turf comprises towing the apparatus behind a small vehicle, such as a tractor, riding lawn mower, or golf cart. The apparatus may be hitched to the back of such vehicle using a hitch. In other embodiments, the step of moving the artificial turf treatment apparatus over the artificial turf comprises pushing the apparatus with a small vehicle, such as tractor, riding lawn mower, or golf cart. The apparatus may be attached to the front end of the vehicle. In various embodiments, the number of passes is from 1 to about 10.

In various embodiments, the method further comprises the step of modifying the surface energy of the plastic surfaces in the artificial turf prior to treatment with an antimicrobial composition. The step comprises moving an artificial turf treatment apparatus further comprising a surface energy treatment module over the artificial turf prior to moving the apparatus over the artificial turf while dispensing antimicrobial composition.

In various embodiments, the method further comprises the step of preconditioning the turf prior to the application of a residual antimicrobial coating composition such as by washing, rinsing and, optionally, sanitizing or disinfecting with conventional products (e.g., peroxide or chlorine bleach).

In various embodiments, the method further comprises the step of applying a titanium species to the artificial turf, such as after application of a residual antimicrobial coating composition. Such a step can seal the antimicrobial coating on the various surfaces of the artificial turf, improving the durability and efficacy of the coating.

Measuring the Efficacy of a Residual Antimicrobial Coating on Various Components of Artificial Turf Measuring the antimicrobial efficacy of an antimicrobial coating can be in a laboratory environment or in the field, or combinations of both, with certain advantages to both. For example, test coupons made of the same plastic used in a component of the artificial turf can be tested under controlled laboratory conditions, such as a coupon made from polyethylene or polypropylene. In non-limiting examples, the coupons may be coated with a residual antimicrobial coating composition, dried, and then inoculated with a test organism to obtain the level of residual antimicrobial efficacy on the dried surface.

In the field, and after an artificial turf treatment apparatus is passed over the artificial turf, any of the various components of the turf can be sampled and brought back to a laboratory for testing. For example, plastic blades of grass can be snipped, and infill material collected and brought back for antimicrobial testing. Qualitative methods can be used at various locations on the artificial turf to check efficiency in the coverage of chemicals across sections of turf.

Testing of a component of artificial turf for pathogens initially present on a playing field can be accomplished by swabbing a surface of the component, such as the plastic blades of grass, with any type of environmental surface sampling and transport swab. Such swabs are usually furnished in a neutralizing buffer and sealed in a vial. The surface under scrutiny is swabbed with the sampling swab, sealed back inside the vial, and then brought to a microbiology laboratory where the sample can be diluted such as through serial dilutions and the latter used to inoculate a number of agar plates. After the agar plates are incubated, the CFU's are counted and a calculation made as the microbial count on the original surface that was swabbed. An exemplary procedure is provided by the CDC, and is entitled "Environmental Hygiene Monitoring—A Guide for Environmental Health Officers," Oct. 5, 2010, Version 3. Measures of pathogen contamination on artificial turf may be obtained and recorded in units of $\log_{10}$ CFU's/cm$^2$, or other suitable units representing number of organisms per unit of surface area. Knowing the species of pathogens present on an actual playing field of artificial turf then informs what organisms to use in controlled antimicrobial testing in the laboratory.

After the artificial turf surfaces are coated with the appropriate residual self-sanitizing coating, the swabbing for pathogens can continue at various locations on the artificial turf. It may be found that previously heavily contaminated and trafficked artificial turf surfaces no longer harbor pathogens, and that pathogens are no longer transferred between individuals interacting on the artificial turf. Depending on the residual antimicrobial coating compositions used on the turf, the coated surfaces may be tested for efficacy of the coating and/or the presence of coating, and recoated as necessary, such as by moving the artificial turf treatment apparatus back over the artificial turf. Retreatment can be performed on a regular schedule for a particular playing field once the durability and efficacy of coatings are determined for the treated playing field.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

I claim:

1. An artificial turf treatment apparatus comprising:
   an agitating module capable of liberating particulate infill material out from the artificial turf and temporarily suspend the particulate infill material above the artificial turf; and
   a spraying module capable of applying a chemical composition onto the particulate infill material while the particulate infill material is temporarily suspended above the artificial turf.

2. The apparatus of claim 1, wherein the agitating module comprises at least one of a broom or a rake.

3. The apparatus of claim 1, wherein the agitating module comprises bristles, tines, or combinations thereof.

4. The apparatus of claim 1, wherein the agitating module comprises a tow-behind or push-in-front sweeper further comprising a rotating drum of bristles.

5. The apparatus of claim 1, wherein the particulate infill material is selected from the group consisting of silica sand, cryogenic rubber, crumb rubber, and combinations thereof.

6. The apparatus of claim 1, wherein the spraying module comprises at least one tank capable of storing and dispensing the chemical composition, a fluidic pump, a spray nozzle, a chemical transfer tubing placing the tank and the fluidic pump in fluidic communication, and a chemical transfer tubing placing the fluidic pump and the spray nozzle in fluidic communication such that the chemical composition is dispensed from the tank and out the spray nozzle when the fluidic pump is operating.

7. The apparatus of claim 1, wherein the chemical composition comprises an organosilane selected from the group consisting of 3-(trimethoxysilyl) propyl dimethyl octadecyl ammonium chloride, 3-(trihydroxysilyl) propyl dimethyl octadecyl ammonium chloride, 3-chloropropyltrimethoxysilane, 3-chloropropyl silanetriol, 3-aminopropyltriethoxysilane, 3-aminopropylsilanetriol, homopolymers thereof, and mixtures thereof.

8. The apparatus of claim 1, wherein the chemical composition comprises a titanium species.

9. The apparatus of claim 1, further comprising a surface energy treatment module capable of decreasing the surface energy of the artificial turf or the particulate infill material, wherein the surface energy treatment module consists of an ozone generator.

10. A method of applying a chemical composition to particles of infill material present in artificial turf, the method comprising liberating the particles out from the artificial turf and spraying the particles with the chemical composition while the particles are temporarily suspended above the artificial turf, wherein the artificial turf comprises synthetic plastic blades of grass bonded to a base material, and wherein the particles of infill material are disposed between the synthetic plastic blades of grass prior to the step of liberating.

11. The method of claim 10, wherein liberating the particles of infill material out from the artificial turf comprises the action of bristles or tines on at least one of the particles and the synthetic plastic blades of grass.

12. The method of claim 11, wherein the action of the bristles or the tines on the particles of infill material further comprises the movement of the bristles or the tines through the synthetic plastic blades of grass of the artificial turf.

13. The method of claim 10, further comprising surface energy treating a portion of a surface of at least one of the synthetic plastic blades of grass, the base material, or the particles of infill material prior to the step of spraying.

14. The method of claim 10, wherein the infill material is selected from the group consisting of silica sand, cryogenic rubber, crumb rubber, and mixtures thereof.

15. The method of claim 10, wherein the chemical composition comprises a residual antimicrobial coating composition.

16. A method of reducing or preventing the transfer of pathogens between individuals interacting on artificial turf, the method comprising moving an artificial turf treatment apparatus over the artificial turf at least one time, the artificial turf treatment apparatus comprising an agitating module capable of liberating particles of infill material out from the artificial turf and temporarily suspending the particles of infill material above the artificial turf, and a spraying module capable of spraying the particles of infill material with a residual antimicrobial coating composition while the particles of infill material are temporarily suspended above the artificial turf.

17. The method of claim 16, wherein the artificial turf comprises synthetic plastic blades of grass bonded to a base material and wherein the particles of infill material are disposed between the synthetic plastic blades of grass.

18. The method of claim 17, wherein the infill material is selected from the group consisting of silica sand, cryogenic rubber, crumb rubber, and combinations thereof.

19. The method of claim 16, wherein the spraying module comprises at least one tank capable of storing and dispensing the residual antimicrobial coating composition, a fluidic pump, a spray nozzle, a chemical transfer tubing placing the tank and the fluidic pump in fluidic communication, and a chemical transfer tubing placing the fluidic pump and the spray nozzle in fluidic communication such that the residual antimicrobial coating composition is dispensed from the tank and out the spray nozzle when the fluidic pump is operating.

20. The method of claim 16, wherein the residual antimicrobial coating composition comprises an organosilane and optionally an organic amine, the organosilane selected from the group consisting of 3-(trimethoxysilyl) propyl dimethyl octadecyl ammonium chloride, 3-(trihydroxysilyl) propyl dimethyl octadecyl ammonium chloride, 3-chloropropyltrimethoxysilane, 3-chloropropylsilanetriol, 3-aminopropyltriethoxysilane, 3-aminopropylsilanetriol, homopolymers thereof, and mixtures thereof.

* * * * *